(12) United States Patent
Orihara et al.

(10) Patent No.: US 8,300,094 B2
(45) Date of Patent: Oct. 30, 2012

(54) IMAGE PICKUP MODULE, MANUFACTURING AND ASSEMBLING METHODS OF THE SAME, ENDOSCOPE AND CAPSULE TYPE ENDOSCOPE USING THE SAME

(75) Inventors: Tatsuya Orihara, Hachioji (JP); Mitsujiro Konno, Hino (JP); Hitoshi Fukuhiro, Atsugi (JP)

(73) Assignee: Olympus Medical Systems Corp., Tokyo (JP)

( * ) Notice: Subject to any disclaimer, the term of this patent is extended or adjusted under 35 U.S.C. 154(b) by 545 days.

(21) Appl. No.: 12/394,159

(22) Filed: Feb. 27, 2009

(65) Prior Publication Data

US 2009/0225157 A1 Sep. 10, 2009

(30) Foreign Application Priority Data

Mar. 6, 2008 (JP) ................................. 2008-056356

(51) Int. Cl.
H04N 7/18 (2006.01)
H04N 5/225 (2006.01)

(52) U.S. Cl. .......................................... 348/76; 348/340

(58) Field of Classification Search ............... 348/76, 348/335, 359, 340, E05.024, E07.085
See application file for complete search history.

(56) References Cited

U.S. PATENT DOCUMENTS

| | | | | |
|---|---|---|---|---|
| 4,973,640 A * | 11/1990 | Matsuda et al. | ............ | 526/323.1 |
| 6,458,308 B1 * | 10/2002 | Kato | ............................. | 264/257 |
| 7,206,126 B2 * | 4/2007 | Endo | ............................. | 359/361 |
| 2003/0011885 A1 * | 1/2003 | Maeda | ......................... | 359/497 |
| 2003/0040259 A1 * | 2/2003 | Umehara et al. | ................. | 451/8 |
| 2003/0067690 A1 * | 4/2003 | Terauchi et al. | ............... | 359/726 |
| 2003/0171649 A1 * | 9/2003 | Yokoi et al. | .............. | 600/109 |
| 2006/0274610 A1 * | 12/2006 | Saito et al. | ................. | 369/13.33 |
| 2007/0055105 A1 * | 3/2007 | Matsuzawa et al. | .......... | 600/176 |

FOREIGN PATENT DOCUMENTS

| | | |
|---|---|---|
| DE | 10 2005 025 528 A1 | 12/2006 |
| JP | 2002-051268 | 2/2002 |
| JP | 2002-118776 | 4/2002 |
| JP | 2002-139662 | 5/2002 |
| JP | 2005-234421 | 2/2005 |
| JP | 2005-152043 | 6/2005 |
| JP | 2007-043628 | 2/2007 |

* cited by examiner

Primary Examiner — Wing Chan
Assistant Examiner — Ruolei Zong
(74) Attorney, Agent, or Firm — Arnold International; Bruce Y. Arnold (57) ABSTRACT

An image pickup module comprises a lens assembly including a lens having a flange part, and a frame component for shading a circumferential surface excluding a neighborhood of a top portion of the flange part in the lens; an image pickup element which the top portion of the flange part touches; and an illumination element arranged around the lens assembly and the image pickup element. The image pickup module is constituted so that exit light from a luminescent surface of the illumination element does not reach directly to an exposed portion that is not shaded by the frame component of the flange part.

26 Claims, 6 Drawing Sheets

IMAGE PICKUP MODULE, MANUFACTURING AND ASSEMBLING METHODS OF THE SAME, ENDOSCOPE AND CAPSULE TYPE ENDOSCOPE USING THE SAME

This application claims benefits of Japanese Patent Application No. 2008-0556356 filed in Japan on Mar. 6, 2008, the contents of which are hereby incorporated by reference.

BACKGROUND OF THE INVENTION

1. Field of the Invention

The present invention relates to an image pickup module having a lens integrated with a flange part, which is used for a personal digital assistant, an endoscope, etc.; a manufacturing method of the image pickup module; an assembling method of the image pickup module; an endoscope using the image pickup module; and a capsule type endoscope using the image pickup module. Particularly, it relates to an image pickup module which is a small and thin, and suitable for an endoscope; a manufacturing method of the image pickup module; an assembling method of the image pickup module; an endoscope using the image pickup module; and a capsule type endoscope using the image pickup module.

2. Description of the Related Art

So far, miniaturization with light weight of the image pickup apparatus used for a cellular phone, an endoscope, etc., especially an image pickup apparatus used for an endoscope etc., has been demanded in order to ease a burden to a patient as much as possible and to improve an operator's handling. Accordingly, it has been equipped with a unit type image pickup module. And in such image pickup module, in order to reduce cost and a manufacture error, it has been proposed that some of lenses which constitute an image pickup module are arranged with a flange part in one, for reducing the number of components, and improving efficiency in assembling. As such image pickup module, there are image pickup apparatuses shown in Publication of the Japanese unexamined patent application, Toku Kai No. 2002-118776, and Publication of the Japanese unexamined patent application, Toku Kai No. 2002-139662, for example.

The image pickup apparatuses shown in the Publication of the Japanese unexamined patent application, Toku Kai No. 2002-118776, and Publication of the Japanese unexamined patent application, Toku Kai No. 2002-139662 are constituted to include a lens having a flange part, and an image pickup unit. The flange part of the lens is engaged to the image pickup unit. At a lower end of the flange part, a gap is formed between it and an upper surface of a substrate, and the lens is attached on the image pickup unit, but not on the substrate. In the image pickup apparatus shown in the Publication of the Japanese unexamined patent application, Toku Kai No. 2002-118776, a resin having a light blocking function is arranged on an upper surface part, an inner side, or an outside part other than the lens part in the lens having a flange part, and it is formed by integrating with the lens part by injection molding. In the image pickup apparatus of the Publication of the Japanese unexamined patent application, Toku Kai No. 2002-139662, a support component formed by a material having a light blocking function is arranged at an upper part of a side of a lens having a flange part.

SUMMARY OF THE INVENTION

The image pickup module according to the present invention is characterized in that in an image pickup module comprising: a lens assembly including a lens having a flange part, and a frame component for shading a circumferential surface excluding a neighborhood of a top portion of the flange part in the lens; and an imaging element which the top portion of the flange part touches; and an illumination element arranged around said lens assembly and said imaging element, it is constituted so that exit light from the luminescence surface of said illumination element may not reach directly to an exposed portion which is not shaded by said frame component of the flange part.

In the image pickup module of the present invention, it is desired that the flange part and the illumination element are arranged so that the exposed portion which is not shaded by said frame component of the flange part may be located at an image side compared with a luminescence surface of said illumination element.

In the image pickup module of the present invention, it is desired that a scope which can illuminate said exposed portion, in said illumination element is shaded by a shading component.

In the image pickup module of the present invention, it is desired that a lens having said flange part, and said image pickup element are fixed by an adhesive by such way that an optical hardening adhesive is arranged at a touching portion where the top portion of the flange part and said image pickup element touch, and light is made enter into the portion where the top portion of the flange part and the image pickup element touch, from a portion between the top portion of said frame component and said image pickup elements.

In the image pickup module of the present invention, it is desired that the portion between the top portion of said frame component and said image pickup elements is sealed with an adhesive having light blocking function.

The image pickup module of the present invention is characterized in that an image pickup module including a lens having a flange part, and an image pickup element which a top portion of the flange part touches comprising: an inner circumferential surface which has an inclined surface and almost mirror surface, wherein it is formed so that a diameter of the surface may become large as it approaches said image pickup element.

In the image pickup module of the present invention, it is desired that the surface coarseness Ra in the inner circumferential surface of said flange part is 1.6 µm or less.

In the image pickup module of the present invention, it is desired that the surface coarseness Ra in the inner circumferential surface of said flange part is 0.2 µm or less.

The image pickup module of the present invention is characterized in that, in an image pickup module that includes a lens having a flange part, and an image pickup element that touches a top portion of said flange part, an inner circumferential surface of said flange part has an inclined surface formed so that a diameter of the inclined surface becomes larger said when approaching said image pickup element, and an angle $\theta$ made by a perpendicular to the inclined surface and an image pickup surface of the image pickup element satisfies the condition $\sin\theta \geq (1/n)$, where n is a refractive index of the lens having said flange part.

In the image pickup module of the present invention, it is desired that a lens having said flange part is manufactured by an injection molding of the resin, and refractive index of said resin is 1.49 or more.

In the image pickup module of the present invention, it is desired that a lens having said flange part is manufactured by an injection molding of the resin, and refractive index of said resin is 1.56 or more.

The manufacturing method of the image pickup module according to the present invention is characterized in that in a manufacturing method of an image pickup module including a lens which has a coated surface and a flange part, and an image pickup element which a top portion of said flange part touches, after the top portion of the flange part in the lens which has the flange part is fixed by touching the image pickup element, a lens surface at the object side of the lens having the flange part is coated.

The assembling method of the image pickup module according to the present invention is characterized in that it comprises a first cutting process for cutting a mark of gate (i.e., a gate mark) that is formed when injection molding is carried out, in the lens having a flange part so that a predetermined length in a radial direction of the lens may remain from the position which does not contain the mark of gate; a touching process for touching (i.e., contacting) a top portion of the flange part to an image pickup element after said first cutting process; and a second cutting process for cutting again said mark of gate.

In the assembling method of the image pickup module according to the present invention, it is desired that said touching process is carried out by such way that said flange part may touch said imaging element, while gripping said mark of gate which was cut so as to remain a predetermined length in the first cutting process.

In the assembling method of the image pickup module according to the present invention, it is desired that it includes a process for attaching a predetermined optical element to the lens having said flange part, between said touching process and said second cutting process.

In the assembling method of the image pickup module according to the present invention, it is desired that it includes a process for attaching a predetermined optical element to the lens having said flange part, between said first cutting process and said touching process.

In the assembling method of the image pickup module according to the present invention, it is desired that cutting of a mark of gate in said first cutting process is carried out at a predetermined position which is separated 1 mm or more from the position which does not contain the mark of gate in the flange part of a lens having said flange part, and cutting of a mark of gate in said second cutting process is carried out at a predetermined position where an amount of projection of the mark of gate from the assembling component of the lens is 0.3 mm or less.

In the assembling method of the image pickup module according to the present invention, it is desired that it includes a process for applying adhesive or paint having light blocking function to a mark of gate after said second cutting process.

The image pickup module according to the present invention is characterized in that in an image pickup module including a lens having a flange part manufactured by an injection molding, and an illumination element arranged around said lens, a cut surface of a mark of gate formed when the injection molding is carried out is cut so that it may be inclined to a surface perpendicular to the direction of a long side of the mark of gate.

In the image pickup module of the present invention, it is desired that an adhesive or paint having light blocking function is applied to said cut surface of the mark of gate.

In the image pickup module according to the present invention, it is desired that in an image pickup module including a lens having a flange part, and an illumination element arranged around said lens, said illumination element is arranged at a position which is off an extension line which joins the center of the lens having said flange part and the center of said mark of gate.

In the image pickup module of the present invention, it is desired that said illumination element is arranged at a position which is off the portion defined between extension lines which join the center of the lens having said flange part and end parts of said mark of gate.

The endoscope according to the present invention is characterized in that any of image pickup modules according to the present invention, an image pickup module manufactured by the manufacturing method according to the present invention, or an image pickup module assembled by any of assembling methods according to the present invention is used.

The capsule type endoscope according to the present invention is characterized in that any of image pickup modules according to the present invention, an image pickup module manufactured by the manufacturing method according to the present invention, or an image pickup module assembled by any of assembling methods according to the present invention is used.

According to the present invention, an image pickup module, a manufacturing method of the image pickup module, an assembling method of the image pickup module, an endoscope using the image pickup module, and a capsule type endoscope using the image pickup module by which a clear image can be obtained can be achieved by preventing from entering of flare and dust.

These and other features and advantages of the present invention will become apparent from the following detailed description of the preferred embodiments when taken in conjunction with the accompanying drawings.

DETAILED DESCRIPTION OF THE PREFERRED EMBODIMENTS

First Embodiment

Figure 1:
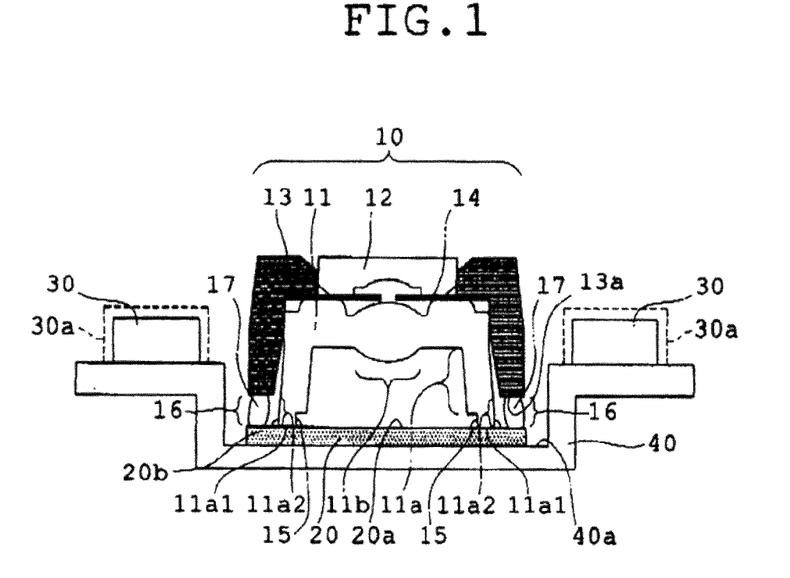
FIG. 1 is an explanatory diagram showing an outlined composition of an image pickup module for concerning a first embodiment according to the present invention

FIG. 1 is an explanatory diagram showing an outlined composition of an image pickup module concerning a first embodiment according to the present invention. The image pickup module of the first applied example is constituted with an image forming lens 10, an image pickup element 20, and an illumination element 30. Here, in FIG. 1, 14 is a brightness aperture stop, 30a is a luminescence surface (luminescence area) of the illumination element, and 40 is a base plate. The image forming lens 10 is constituted with lenses 11 and 12 and a frame component 13.

The lens 11 is manufactured by an injection molding, and equipped with a flange part 11a and a lens part 11b which are formed in one. A gate used at the time of an injection molding is arranged at a position near the image pickup element 20 in the flange part 11a, and a mark of the gate (illustration is not shown) remains at a position corresponding to the gate in the flange part 11a. The frame component 13 is manufactured with a material having light blocking function. Here, the frame component 13 is arranged so that it may hold a predetermined portion of an outer peripheral portion of lenses 11 and 12, and may carry out positioning of the lens 12 to the lens 11, and may cover almost all the outer peripheral portion of the lenses 11 and 12 except vicinity of a top portion of the flange part 11a in the lens 11.

Then image forming lens 10 is an assembly component which is formed by combining lenses 11 and 12 and the frame component 13. Here, as for the image forming lens 10, its constitution is not limited to a constitution which consists of two lenses 11 and 12, but may consist of three or more lenses. In this case, what is necessary is to constitute that a lens nearest to an image pickup element is made as the lens 11 having the flange part 11a like the lens 10. The top portion 11a1 of the flange part 11a touches the image pickup element 20. The illumination element 30 is arranged around the image forming lens 10 and the image pickup element 20.

The base plate 40 holds the illumination element 30 and the image pickup element 20. The base plate 40 is dented at a part 40a which holds the image pickup element 20, and an exposed part 11a2 which is not shaded by the frame component 13 in the flange part 11a is located near an image side compared with the luminescence surface (luminescence area) 30a of the illumination element 30. By this way, it is constituted so that light emanated from the luminescence surface 30a of the illumination element 30 may not reach directly to the exposed portion 11a2 which is not shaded by the frame component 13 of the flange part 11a.

An optical hardening adhesive 15 intervenes at a touching portion where the top portion 11a1 of the flange part 11a touches the image pickup element 20. And, by making light enter into the touching portion where the top portion 11a1 of the flange part 11a touches the image pickup element 20 through a portion between the top portion 13a of the frame component 13, and the image pickup elements 20, a lens having the flange part 11a and the image pickup element 20 are fixed by the adhesive. Moreover, the exposed portion 16 between the top portion 13a of the frame component 13 and an edge part 20b of the image pickup element 20 is sealed with the adhesive 17 having light blocking function, which is blended with black paint.

According to the image pickup module of the first embodiment constituted in this way, since the light emitted from the luminescence surface 30a of the illumination element 30 does not reach directly the exposed part 11a2 in the flange part 11a, flare can be prevented. By making light enter into the touching portion where the top portion 11a1 of the flange part 11a touches the image pickup element 20 from an exposed part 16 between the top portion 13a of the frame component 13 and the edge part 20b of the image pickup elements 20 prior to carrying out sealing with the adhesive 17 having light blocking function, which is blended with black paint, the lens 11 having the flange part 11a can be fixed directly to the image pickup element 20. Accordingly, for example, shifting of focusing position does not occur by a clearance of a frame component and a lens component like in the case of cementing a frame component and an image pickup element, and moreover, fixing can be made in a short time.

Furthermore, since the exposed area 16 between the top portion 13a of the frame component 13 and the image pickup element 20 is sealed with the adhesive 17 having light blocking function, the exposed part 11a2 is shaded, and since the light which was emitted from the illumination element 30 and scattered by reflection by other components (frame component, base plate, etc.) can be shaded, flare can be prevented more certainly. Furthermore, in the image pickup module of the first embodiment, it is arranged so that the light emitted from the luminescence surface 30a of the illumination element 30 may not reach directly the exposed part 11a2 in the flange part 11a, and strong light may not enter. Therefore, even if an adhesive having light blocking function is translucence, a sufficient flare prevention effect can be obtained.

Second Embodiment

Figure 2:
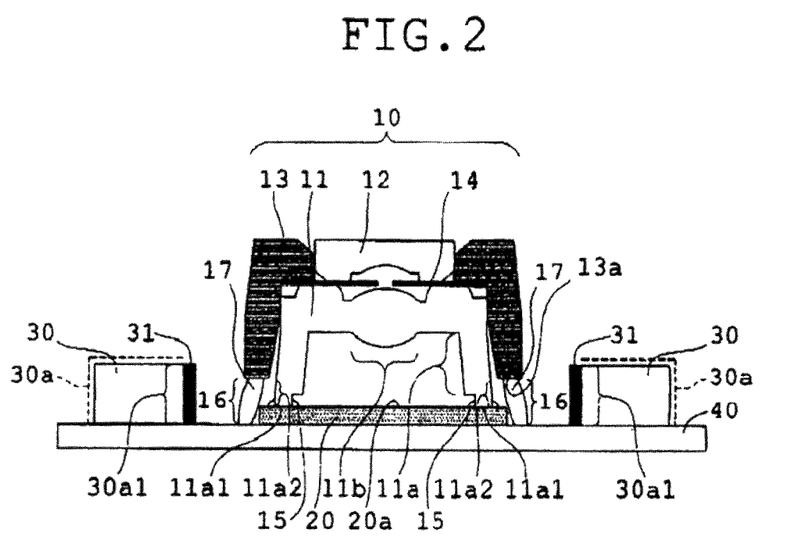
FIG. 2 is an explanatory diagram showing an outlined composition of an image pickup module concerning a second embodiment according to the present invention.

FIG. 2 is an explanatory diagram showing an outlined composition of an image pickup module concerning the second embodiment according to the present invention. In the image pickup module of the second embodiment, a base plate 40 is formed as a plane that holds the image pickup element 20 and the illumination element 30 at the same level, and an exposed part 11a2 which is not shaded by a frame component 13 in a flange part 11a is located nearly at the same position to a luminescence surface (luminescence area) 30a of the illumination element 30 as seen in the image pickup module of the first embodiment. Instead of this, in the image pickup module of the second embodiment, a portion 30a1 which could illuminate the exposed part 11a2 in the illumination element 30 is shaded by a shading component 31. By this way, it is constituted so that the light emanated from the luminescence surface 30a of the illumination element 30 may not reach directly to the exposed portion 11a2 which is not shaded by the frame component 13 of the flange part 11a. Further, a portion between a top portion 13a of the frame component 13, and a perimeter of the image pickup elements 20 is sealed with an adhesive 17 having light blocking function, which is blended with black paint. The other constitutions are almost same to those of the image pickup module of the first embodiment.

According to the image pickup module of the second embodiment constituted in this way, the light which goes toward the exposed part 11a2 in the flange part 11a from the illumination element 30 is shaded by the shading component 31. Therefore, flare can be prevented since the light emitted from the luminescence surface 30a of the illumination element 30 does not reach directly the exposed part 11a2 in the flange part 11a.

Other functions and effects are almost the same to those in the image pickup module of the first embodiment.

Third Embodiment

Figure 3:
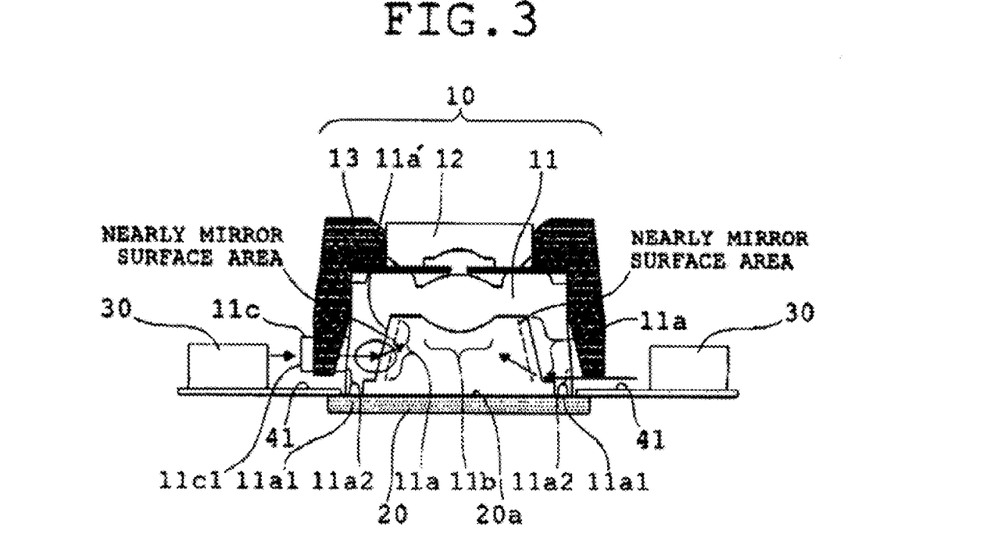
FIG. 3 is an explanatory diagram showing an outlined composition of an image pickup module concerning a third embodiment according to the present invention.

FIG. 3 is an explanatory diagram showing an outlined composition of an image pickup module concerning a third embodiment according to the present invention. In the image pickup module of the third embodiment, an image pickup element 20 and an illumination element 30 are mounted on a supporting plate 41, respectively, where they are arranged on nearly the same plane. Moreover, a frame component 13 is formed so that a mark of gate 11c formed on the outer circumferential surface of a flange part 11a may be passed, and the mark of gate 11c is exposed to the exterior of the frame component 13. Accordingly, it is constituted so that the exit light emanated from the luminescence surface of the illumination element 30 may reach directly to the exposed portion 11a2 which is not shaded by the frame component 13 of the flange part 11a, and an end surface 11c1 of the mark of gate 11c. Instead of such constitution mentioned above, in the image pickup module of the third embodiment, it is constituted such that an inner circumferential surface 11a' of the flange part 11a has an inclined surface is formed so that a diameter of the surface may become large as it approaches the image pickup element 20, and it has a nearly mirror surface with coarseness Ra that is 1.6 μm or less.

According to the image pickup module of the third embodiment constituted in this way, the exit light from the luminescence surface of the illumination element 30 enters into the end surface 11c1 of the exposed part 11a2 which is not shaded by the frame component 13, and the mark of gate 11c. The light which goes in nearly parallel to the image pickup surface 20a of the image pickup element 20, out of the entered light, reaches the inner circumferential surface 11a' of the flange part 11a without being refracted mostly on an incidence surface and decreasing its intensity. However, as mentioned above, it is constituted such that the inner circumferential surface 11a' of the flange part 11a has an inclined surface which is formed so that a diameter of the surface may become large as it approaches the image pickup element 20, and it is formed to be an almost mirror surface. Accordingly, the light which reached the inner circumferential surface 11a' is refracted in the direction which is apart from the image pickup surface 20a of the image pickup element 20, without being mostly scattered, when emitted from the inner circumferential surface 11a'. Therefore, the light from the source part 30 does not enter into the image pickup surface 20a of the image pickup element 20, and thus flare can be prevented.

Here, if surface coarseness Ra of the inner circumferential surface 11a' is 1.6 μm or less, smooth surface finishing is obtained, and the scattering light from the exit surface decreases. Accordingly, it can be regarded as an almost mirror surface. It is desired that surface coarseness Ra of the inner circumferential surface 11a' is 0.2 μm or less, since the intensity of scattering light decreases further to an intensity which can be almost disregard.

Fourth Embodiment

Figure 4:
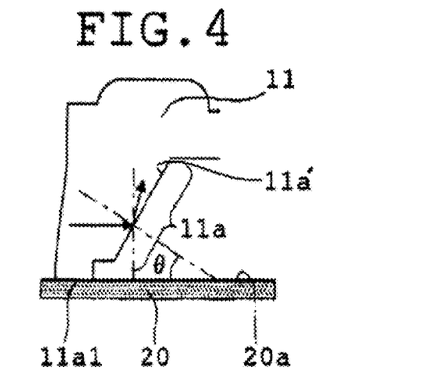
FIG. 4 is an explanatory diagram showing a composition of a principal part of an image pickup module concerning a fourth embodiment according to the present invention.

FIG. 4 is an explanatory diagram showing a composition of a principal part of an image pickup module concerning a fourth embodiment according to the present invention.

In the image pickup module of the fourth embodiment, it is constituted such that an inner circumferential surface 11a' of the flange part 11a has an inclined surface is formed so that a diameter of the surface may become large as it approaches the image pickup element 20, and an angle θ made by a perpendicular to the inclined surface and an image pickup surface 20a of the image pickup element 20 is $\sin^{-1}$ (1/n) or more (n is refractive index of the lens having the flange part 11a).

The other constitutions are almost same to those of the image pickup module in the third embodiment.

As explained above, the light which reaches the inner circumferential surface 11a' of the flange part 11a without being mostly refracted on an incidence surface, and decreasing its intensity is the light which goes in nearly parallel toward the image pickup surface 20a of the image pickup element 20, out of the light which entered into the exposed part 11a2 which is not shaded by the frame component 13, and the end surface 11c1 of the mark of gate 11c. However, according to the image pickup module of the fourth embodiment, it is constituted with a surface that has an inclined surface formed so that a diameter of the surface may become large as it approaches the image pickup element 20, wherein an angle θ made by a perpendicular to the inclined surface and an image pickup surface 20a of the image pickup element 20 is $\sin^{-1}$ (1/n) or more (n is refractive index of the lens 11 having the flange part 11a). If the inclined surface having such angle is used, the light which enters into the inside of the flange part 11a, and goes on parallel with it, does not exit from an inner circumferential surface 11a' of the flange part 11a, and is reflected by the inner circumferential surface 11a'. Accordingly, the light dose not enter into the image pickup surface 20a, and flare can be prevented.

In the injection molding of the lens 11 having the flange part 11a as a resin material, for example, acrylics (refractive index is about 1.49), cyclo olefin polymer (refractive index; about 1.5 to 1.53), polycarbonate (refractive index; about 1.58 to 1.65), and amorphous polyester copolymer resin (refractive index; about 1.6 to 1.63) can be used. However, for example, in the injection molding of the lens 11 having the flange part 11a, by using a resin having refractive index of 1.49, it is good if the angle θ made by the perpendicular to the inclined surface of the inner circumferential surface 11a' of the flange part 11a and the image pickup surface 20a of the image pickup element 20 is made so as to become 42.2° or more. (namely, it is good if the angle made by the inclined surface of inner circumferential surface 11a' of the flange part 11a and the image pickup surface 20a of the image pickup element 20 is made so that it may become less than 47.8°).

Furthermore, for example, in the injection molding of the lens 11 having the flange part 11a, by using a resin having refractive index of 1.56, it is good if the angle θ made by the perpendicular to the inclined surface of the inner circumferential surface 11a' of the flange part 11a and the image pickup surface 20a of the image pickup element 20 is made so as to become 39.9° or more (namely, the angle made by the inclined surface of inner circumferential surface 11a' of the flange part 11a and the image pickup surface 20a of the image pickup element 20 is made so that it may become less than 40.1°). Furthermore, for example, in the injection molding of the lens 11 having the flange part 11a, by using a resin having refractive index of 1.65, it is good if the angle θ made by the perpendicular to the inclined surface of the inner circumferential surface 11a' of the flange part 11a and the image pickup surface 20a of the image pickup element 20 is made so as to become 37.3° or more (namely, the angle made by the inclined surface of the inner circumferential surface 11a' of the flange part 11a and the image pickup surface 20a of the image pickup element 20 is made so that it may become less than 42.7°).

In order to miniaturize the lens 11 having the flange part 11a, it is desired that the angle of inclination of the inner circumferential surface 11a' of the flange part 11a (namely, the angle made by the perpendicular to the image pickup surface 20a of the image pickup element 20 and the inclined surface of inner circumferential surface 11a' of the flange part 11a) is made small as much as possible. Here, the angle of inclination of the inner circumferential surface 11a' of the flange part 11a is equal to the angle θ made by the perpendicular to the inclined surface of the inner circumferential surface 11a' of the flange part 11a and the image pickup surface 20a of the image pickup element 20.

As explained above, if a resin having refractive index of 1.56 or more is used, the angle θ made by the perpendicular to the inclined surface of the inner circumferential surface 11a' of the flange part 11a and the image pickup surface 20a of the image pickup element 20 can be made so as to become below 40 (for example, when a resin with refractive index of 1.56 is used, the angle θ can be 39.9°≦θ<40°; for example, when a resin with refractive index of 1.65 is used, the angle θ can be 37.3≦θ<40°).

It becomes advantageous for miniaturizing of the injection molding of the lens 11 having the flange part 11a.

Fifth Embodiment

Figure 5:
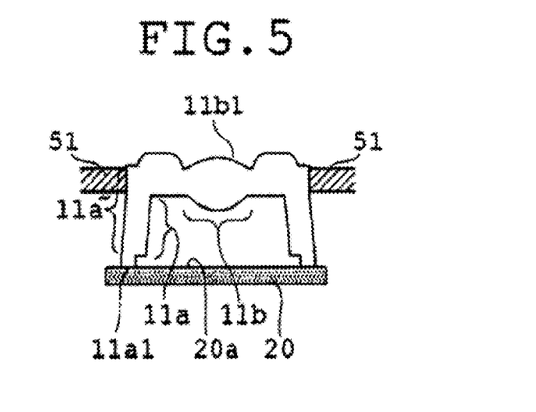
FIG. 5 is an explanatory diagram showing a principal part of a manufacturing method of an image pickup module concerning a fifth embodiment according to the present invention.

FIG. 5 is an explanatory diagram showing a principal part of a manufacturing method of an image pickup module concerning a fifth embodiment according to the present invention. The manufacturing method of the image pickup module of the fifth embodiment includes the following steps. First, the top portion 11a1 of the flange part 11a in the lens 11 having the flange part 11a is made touch the image pickup surface 20a of the image pickup element 20, and fixed by using optically hardening adhesives, etc. (illustration is not shown). Thereby, a surface directed toward the surface of the image pickup element 20 in the lens 11 having the flange part 11a, and the image pickup surface 20a of the image pickup element 20 become in a state that are isolated from the open air.

Then, a surface 11b1 at the object side in the lens part 11b of the lens 11 having the flange part 11a is coated. In details, for example, as shown in FIG. 5, a coating work holder 51 is arranged at a part nearest to the lens part 11b in outer circumferential surface 11a" of the flange part 11a in the lens 11 having the flange part 11a which is fixed by touching of the top portion 11a1 and the image pickup element 20. Then, coating is carried out onto the surface 11b1 at the object side in the lens part 11b, by a predetermined resin, and the like in order to strengthen functions as a lens (for example, improvement of scratch prevention, acid resisting, manufacturing ultraviolet ray cut, shock-proof, etc.).

According to the image pickup module of the fifth embodiment, since the coating is carried out after having sealed the image pickup surface 20a of the image pickup element 20 via the flange part 11a of the lens 11, the dust generated at the time of coating does not adheres to a surface of the lens 11, which is directed toward the image pickup element 20. Therefore, fall of the dust generated at the time of coating on the image pickup surface 20a does not occur, and a good quality image without reflection by dust can be obtained.

Sixth Embodiment

Figures 6A, 6B:
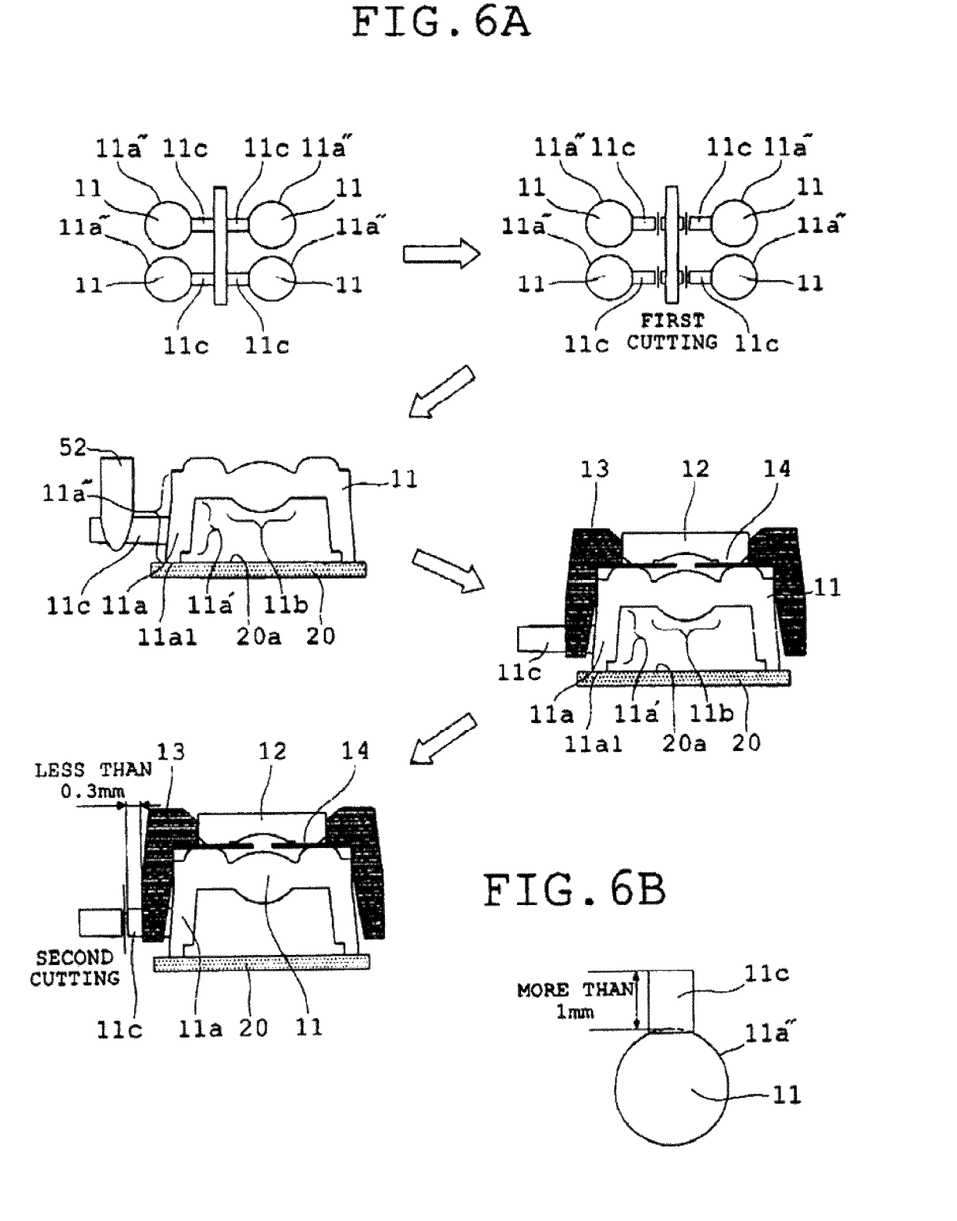
FIGS. 6A and 6B are explanatory diagrams showing an assembling method of an image pickup module concerning a sixth embodiment according to the present invention, where steps of the assembling process, and a cut position of a mark of gate in the first cutting process in the assembling process are shown, respectively.

FIGS. 6A and 6B are explanatory diagrams showing an assembling method of an image pickup module concerning a sixth embodiment according to the present invention, wherein steps of assembling process, and a cut position of a mark of gate in a first cutting process in the assembling process is shown, respectively.

The assembling of the image pickup module by the assembling method of the image pickup module of the sixth embodiment is carried out by steps shown in FIG. 6A. First, a lens 11 having a flange part 11a is manufactured by injection molding. At the time of the injection molding, the mark of gate (or gate mark) Hc is connected with a part of an outer circumferential surface 11a" of the flange part 11a in the lens 11. And then, the mark of gate 11c is cut at a position where a predetermined length remains from a position which does not contain the mark of gate 11c in the flange part 11a. That is, as shown in FIG. 6B, a part which is apart from the outer circumferential surface 11a" of the flange part 11a in the mark of gate Hc is cut (first cutting). In this case, it is desired that cutting is carried out at a part apart from the outer circumferential surface 11a" by 1 mm or more, so that gripping of the gate part Hc through a gripping component 52 (mentioned later) can be insured.

And then, the top portion 11a1 of the flange part 11a is made touch the surface of the image pickup element, and fixed by using optically hardening adhesives, etc. (illustration is not shown). Touching is carried out by gripping the mark of gate 11c that remains in the flange part 11a, using the gripping component 52. Here, the touching may be carried out in such way that while holding or adsorbing the outer circumferential surface 11a" of the flange part 11a by using a holding means, or an adsorption means that is not illustrated, it is made touch the image pickup surface 20a of the image pickup element 20. And then, other optical elements such as a frame component 13, a lens 12 combined with the lens 11 having the flange part 11a, etc., are attached to the lens 11 having the flange part 11a. Then, the mark of gate 11c is cut again (second cutting). At this time, if the mark of gate 11c remains too much, whole of the lens 11 having the flange part 11a will become large, and, consequently, the whole image pickup module becomes large. In a product such as an endoscope for which miniaturization is required, it is desired that an amount of projection of the mark of gate 11c from the assembling component of a lens constituting an image pickup module (here, an amount of projection of the mark of gate 11c from the outer circumferential surface of the frame component 13) is 0.3 mm or less.

According to the assembling method of the sixth embodiment, since the cutting of the mark of gate 11c (second cutting) is carried out after sealing the image pickup surface 20a of the image pickup element 20 via the flange part 11a of the lens 11, dusts generated at the time of cutting of the mark of gate 11c, which adhere to a surface at the side of the image pickup element 20 of the lens 11 having the flange part 11a become less. Therefore, dusts generated at the time of cutting of the mark of gate 11c do not fall on the image pickup surface 20a, and a good quality image without reflection image by dusts can be obtained. Although, the mark of gate 11c is cut also in the first cutting, in the first cutting, since the cutting is carried out at the predetermined position which is apart from the outer circumferential surface 11a" of the flange part 11 in the mark of gate 11c, it is possible to prevent dusts generated at the time of cutting of the mark of gate 11c from reaching a surface at the side of the image pickup element 20 of the lens 11 having the flange part 11a. Furthermore, since the touching of the image pickup element 20 and the top portion 11a1 of the flange part 11a is carried out while gripping the mark of gate 11c, the lens part 11b is not contacted, and scratching of a lens surface does not occur.

In an example of FIG. 6, assembling is carried out in the following steps; after the first cutting, the top portion 11a1 of the flange part 11a is made touch the image pickup element 20, and then, predetermined optical elements (the frame component 13, the lens 12 etc.) are attached to the lens 11 having the flange part 11a. However, the following steps may be carried out after attaching the predetermined optical elements (the frame component 13, the lens 12, etc.) to the lens 11 having the flange part 11a, the top portion 11a1 of the flange part 11a is made touch the image pickup element 20. Furthermore, it is desired that an adhesive or paint having light blocking function is applied on the exposed part of the mark of gate 11c. By this way, the light from the illumination element 30 is shaded, and it becomes easy to prevent flare.

Seventh Embodiment

Figures 7, 8:
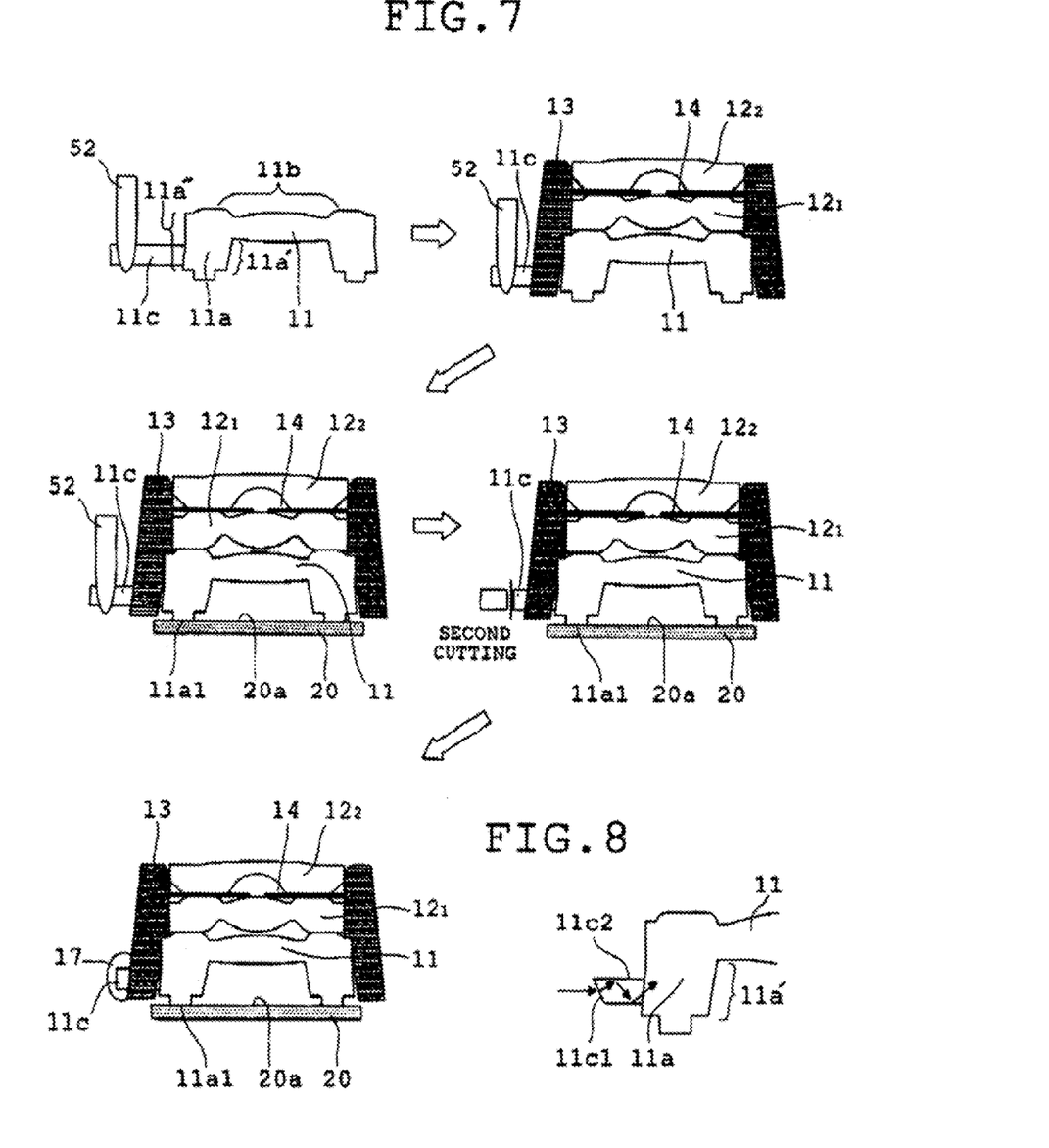
FIG. 7 is an explanatory diagram showing steps of an assembling process of a principal part in the assembling method of the image pickup module concerning a seventh embodiment of the present invention.
FIG. 8 is an explanatory diagram showing a composition of a principal part of an image pickup module concerning an eighth embodiment according to the present invention.

FIG. 7 is a diagram showing steps of the assembling process of the principal part in the assembling method of the image pickup module concerning the seventh embodiment of the present invention. The assembling method of the image pickup module of the seventh embodiment is a modification of the assembling method of the image pickup module of the sixth embodiment, and steps after the first cutting differ from those of the sixth embodiment, as shown in FIG. 7. In the assembling method of the image pickup module of the seventh embodiment, after the first cutting, a mark of gate 11c which has a remaining portion by a predetermined length from the position which does not include the mark of gate 11c in the flange part 11a is gripped by a gripping component 52. Then, other components such as a frame component 13, a lens 12 to be combined with the lens 11 having the flange part 11a, etc., are attached to the lens 11 having the flange part which is being gripped by the gripping component 52. Then, while the mark of gate 11c in the attached component is gripped by the gripping component 52, the top part 11a1 of the flange part 11a is made touch the image pickup surface 20a of the image pickup element 20, and then, it is made fix by using an adhesive, such as an optical hardening adhesive which is not illustrated. Then, the mark of gate 11c is again cut like the assembling method of the image pickup module in the sixth embodiment (second cutting). Then, an adhesive 17 or paint (illustration is not shown) having light blocking function is applied to an exposed portion of the mark of gate 11c.

According to the assembling method of the image pickup module of the seventh embodiment, like the assembling method of the image pickup module of the sixth embodiment, since the mark of gate 11c is cut after sealing the image pickup surface 20a of the image pickup element 20 via the flange part 11a of the lens 11 (second cutting), dusts generated at the time of cutting of the mark of gate 11c does not adhere to a surface at the side of the image pickup element of the lens having the flange part. Consequently, dusts generated at the time of cutting of the mark of gate 11c does not fall to the image pickup surface, and accordingly a good quality image without reflection image by dust can be obtained. Here, although the mark of gate 11c is cut also in the first cutting, in the first cutting, since the mark of gate 11c is cut at a position which is apart at a predetermined length from outer circumferential surface 11a" of the flange part 11a in the mark of gate 11c, dusts generated at the time of cutting the mark of gate 11c can be prevented from reaching the surface at the side of the image pickup element 20 of the lens 11 having the flange part 11a.

Furthermore, since the other optical components are attached, and the image pickup element 20 is made touch the top part 11a1 of the flange part 11a while gripping the mark of gate 11c, the lens part 11b is not contacted, and no scratch is attached to a lens surface. Moreover, since an adhesive or paint having light blocking function is applied to the exposed part of the mark of gate 11c, the light from the illumination element 30 is shaded, and accordingly it becomes easy to prevent flare.

Eighth Embodiment

FIG. 8 is a diagram showing a composition of the principal part of the image pickup module concerning the eighth embodiment of the present invention. As for the image pickup module of the eighth embodiment, in an image pickup module including a lens 11 having a flange part 11a manufactured by an injection molding, and an illumination element (not illustrated) arranged around the lens 11, a cut surface (end surface 11c1) of a mark of gate 11c formed at the time of injection molding is cut so that it may incline to a surface perpendicular to the direction of a long side of the mark of gate 11c. Therefore, most of the light which enters into the mark of gate 11c enters obliquely to the cut surface 11d1 of the mark of gate 11c. The light which entered obliquely to the cut surface 11d1 of the mark of gate 11c is refracted in the cut surface 11d1 of the mark of gate 11c, and enters into the side surface 11c2 of the mark of gate 11c, and is reflected repeatedly on the side surface 11c2 of the mark of gate 11c. Moreover, a part of the light which enters into the mark of gate 11c enters perpendicularly to the cut surface 11d1 of the mark of gate 11c. At this time, the cut surface 11d1 of the mark of gate 11c inclines to the cut surface 11c1 of the mark of gate 11c. Accordingly, the light which entered perpendicularly to the cut surface 11d1 of the mark of gate 11c passes the cut surface 11d1 of the mark of gate 11c, and enters into the side surface 11c2 of the mark of gate 11c, and is reflected repeatedly on the side surface 11c2 of the mark of gate 11c.

Thus, all of the light which entered perpendicularly to the cut surface 11d1 of the mark of gate 11c passes the cut surface 11d1 of the mark of gate 11c, and then is reflected repeatedly on the side surface 11c2 of the mark of gate 11c. Thereby, scattering light having decreased intensity enters into the flange part 11a. However, as explained above, the light which reaches the inner circumferential surface 11a' of the flange part 11a without mostly decreasing its intensity is the light which goes in nearly parallel to the image pickup surface 20a of the image pickup element 20, out of the light which enters into an exposed part 11a2 which is not shaded by a frame component, and the end surface 11d1 of the mark of gate 11c, and its intensity decreases further during the time that scattered light reaches the inner circumferential surface 11a'. Consequently, the light emitted from the inner circumferential surface 11a' of the flange part 11a becomes very slight and weak light, and hardly enters into the image pickup surface 20a. Therefore, flare is reduced.

Here, it is desired that an adhesive or paint having light blocking function is applied to the cut surface 11c1 of the mark of gate 11c. By this way, the light from the illumination element 30 is shaded, and flare can be prevented more certainly. In the image pickup module of the present embodiment, by obliquely cutting of the cut surface 11c1 of the gate part 11c as mentioned above, an effect that weakens the intensity of the light from the illumination element 30 is obtained. Accordingly, if an adhesive or paint having light blocking function applied to the cut surface 11c1 of the mark of gate 11c has translucence property as a light blocking function, sufficient effect of flare prevention can be obtained.

Ninth Embodiment

Figure 9:
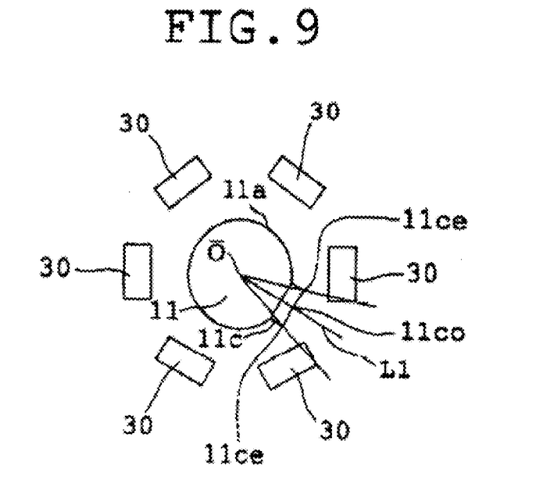
FIG. 9 is an explanatory diagram showing a composition of a principal part of an image pickup module concerning a ninth embodiment according to the present invention.

FIG. 9 is an explanatory diagram showing a composition of a principal part of an image pickup module concerning a ninth embodiment according to the present invention. As for the image pickup module of the eighth embodiment, in an image pickup module including a lens 11 having a flange part 11a manufactured by injection molding, and an illumination element 30 arranged around the lens 11, the illumination element 30 is arranged at a position which is off extension line L1 which joins the center O of the lens 11 having the flange part 11*a,* and the center 11*co* of the mark of gate 11*c*. In FIG. 9, lice is an end of the mark of gate 11*c* according to the image pickup module of the ninth embodiment, since the light having strong intensity from the illumination element 30 hardly enters into the mark of gate 11*c,* flare can be prevented.

Tenth Embodiment

Figure 10:
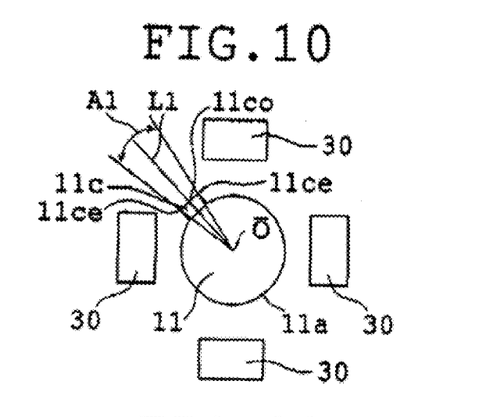
FIG. 10 is an explanatory diagram showing a composition of a principal part of an image pickup module concerning a tenth embodiment according to the present invention.
Figure 11:
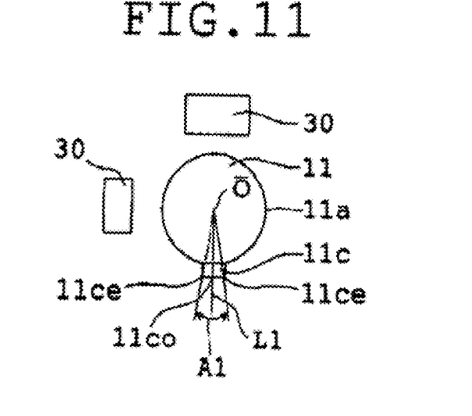
FIG. 11 is an explanatory diagram showing a composition of a principal part of an image pickup module concerning a modified embodiment of the FIG. 10.

FIG. 10 is an explanatory diagram showing a composition of a principal part of an image pickup module concerning a tenth embodiment according to the present invention. FIG. 11 is an explanatory diagram showing a composition of a principal part of an image pickup module concerning a modified example of the FIG. 10. In the image pickup module of the tenth embodiment, and its modified example, in an image pickup module including a lens 11 having a flange part 11*a* manufactured by injection molding, and an illumination element 30 arranged around the lens 11, an illumination element 30 is arranged at a position which is off a portion A1 defined by extension lines which join the center O of the lens 11 having the flange part 11*a,* and end portions 11*ce* of the mark of gate 11*c*. According to the image pickup module of the tenth embodiment, since the light which enters into the mark of gate 11*c* from the illumination element 30 is restricted further, flare can be prevented more certainly.

The image pickup module of the present invention is not limited to each constitution of each of embodiment mentioned above, and it is more desired that any constitutions of embodiments are combined arbitrarily. If constitutions of embodiments are combined, the effect in each of embodiments are synergistically demonstrated, and accordingly much clearer image can be obtained. Effects of the image pickup module of each of embodiments explained above become particularly remarkable, when it is used for the optical apparatus such as a capsule endoscope, a common endoscope, etc., for which miniaturization is required.

Next, examples of constitution of the endoscope using the image pickup module according to the present invention will be shown.

Eleventh Embodiment

Figure 12:
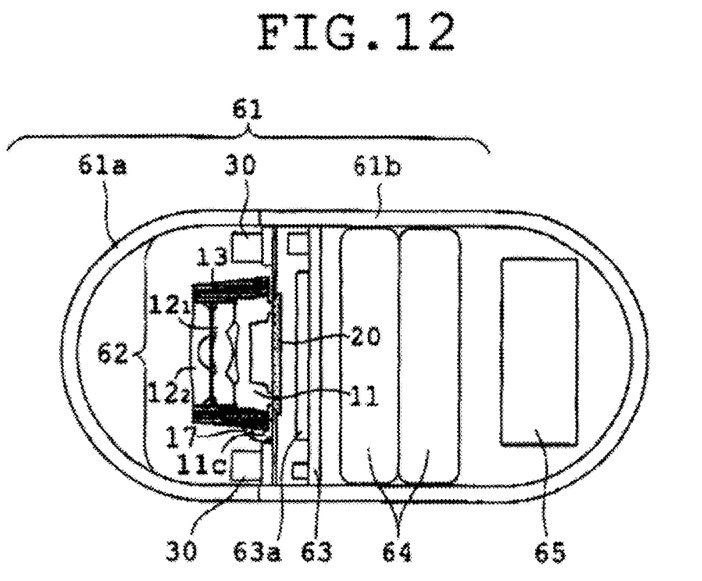
FIG. 12 is a sectional view showing an outlined composition of a capsule type endoscope using the image pickup module concerning an eleventh embodiment according to the present invention.

FIG. 12 is a sectional view showing an outlined composition of a capsule type endoscope using the image pickup module concerning the eleventh embodiment according to the present invention. The capsule endoscope of FIG. 12 has an image pickup module 62, a control substrate 63, a battery 64, and a radio apparatus 66 in a capsule 61 consisting of a transparent cover 61*a* and a housing 61*b* for the main part of the endoscope. The transparent cover 61*a* is formed in nearly hemisphere form, and arranged at the top of the housing 61*b* for the main part of the endoscope. The image pickup module 62 is constituted as same as the image pickup module assembled by the assembling method of the image pickup module according to the seventh embodiment, and arranged inside of the transparent cover 61*a*. As the image pickup module 62, any image pickup module in each of embodiments mentioned above, the image pickup module manufactured by the manufacturing method, or the image pickup module assembled by the assembling method in the embodiments mentioned above may be used.

On the control substrate 63, circuits 63*a* including a circuit for driving and controlling a light emitting element 30 arranged at the image pickup module 62, a circuit for driving and controlling an image pickup element 20 arranged at the image pickup module 62, a circuit for generating an image signal from a signal picked up by the image pickup element 20, and a circuit for driving and controlling the radio apparatus 65, etc., are arranged. The battery 64 supplies electric power to the image pickup element 20, each of circuits in and the control substrate 63, and the radio apparatus 65, etc. The radio apparatus 65 transmits the signal picked up by the image pickup element 20, and the image signal generated by the image signal generating circuit, as electric waves, to an external receiving apparatus.

Twelfth Embodiment

Figure 13:
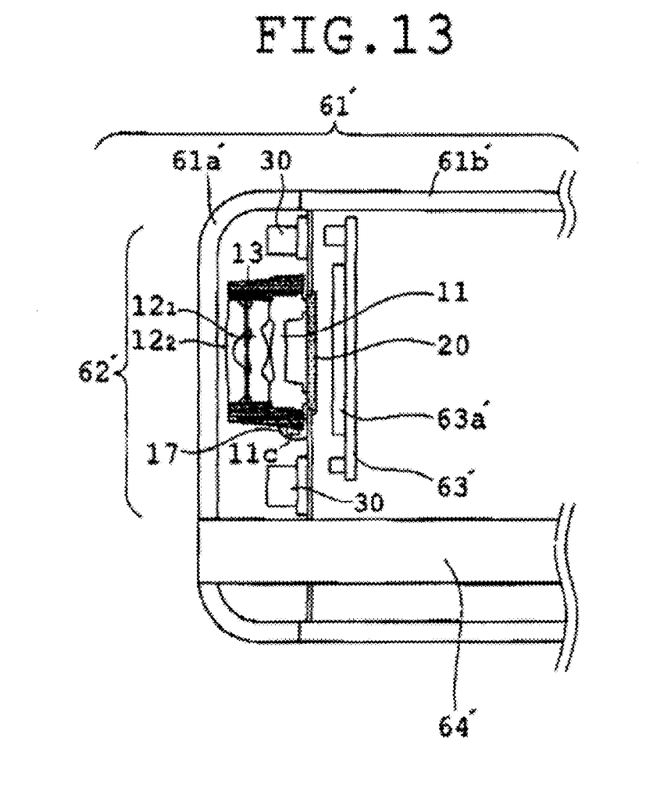
FIG. 13 is a sectional view showing an outlined composition of an endoscope having the image pickup module concerning a twelfth embodiment according to the present invention.

FIG. 13 is a sectional view showing an outlined composition of an endoscope having the image pickup module concerning the twelfth embodiment according to the present invention. The endoscope of the twelfth embodiment has an image pickup module 62', and a control substrate 63' in a top-insertion-part 61' consisting of a transparent cover 61*a'* and a housing 61*b'* for the main part of the endoscope. In FIG. 13, 64' is a forceps hole. The transparent cover 61*a'* is formed in semi-cylindrical form, and arranged at the top of the housing 61*b* for the main part of the endoscope. The image pickup module 62', is constituted as same as the image pickup module assembled by the assembling method of the image pickup module according to the seventh embodiment shown in FIG. 7, and arranged inside of the transparent cover 61*a'*. Here, in the image pickup module 62, any of the image pickup module, the image pickup module manufactured by the manufacturing method of the image pickup module, or the image pickup module assembled by the assembling method of the image pickup module in each of embodiments mentioned above can be used. The control substrate 63 has circuits, etc., 63*a'* including a circuit for driving and controlling a light emitting element 30 arranged at the image pickup module 62', a circuit for driving and controlling an image pickup element 20 arranged at the image pickup module 62', and a circuit for producing an image signal from the signal picked up by the image pickup element 20.

In a small observation apparatus like an endoscope, in particular, an apparatus for observing a digestive organ inside of a human body, such as a capsule endoscope, an effect of reduction of burden of a patient becomes very large by miniaturizing, even if its amount is very small. Accordingly, in endoscope, in particular, capsule endoscope, it is desired that it is constituted that in order to make the whole diameter thin as much as possible, the lens having a flange part is made touch the image pickup element on the nearly same plane, while small illumination elements (LED) are annularly arranged to the perimeter. However, if it is constituted as mentioned above, problems such as flare light, mixing of dusts as mentioned above are easily generated. Accordingly, a clear image is hard to be obtained. However, according to the capsule endoscope, and the endoscope of eleventh embodiment and twelfth embodiment shown in FIG. 12 and FIG. 13, entering of flare and dust are prevented, and a clear image can be obtained since the image pickup module of the present embodiments is used.

The endoscope using the image pickup module, the manufacturing method of the image pickup module, the assembling method of the image pickup module, the endoscope using the image pickup module, the capsule type endoscope and the image pickup module according to the present invention is useful in fields where an observation apparatus equipped with a small image pickup element, for example, a capsule endoscope, a common endoscope, etc., to which miniaturization and high preciseness are required is manufactured and used.

What is claimed is:

1. An image pickup module comprising:
    a lens having a flange part, said lens and flange part being integrally formed of a light transmitting material, and an image pickup element which a top portion of the flange part touches;
    a frame component that forms a lens assembly together with the lens having the flange part, the frame component being constructed and arranged to shade an outer circumferential surface of the lens excluding a neighborhood of the top portion of the flange part; and
    illumination elements arranged around the lens assembly and the image pickup element; wherein
    the image pickup module is constructed and arranged so that light emergent from light-emitting surfaces of the illumination elements fails to directly reach an exposed portion, which fails to be shaded by the frame component, of the flange part, and
    an inner circumferential surface of the flange part has an inclined surface such that a diameter of the inner circumferential surface becomes larger as the inclined surface approaches said image pickup element.

2. The image pickup module according to claim 1, wherein the surface coarseness Ra of the inner circumferential surface of said flange part is 1.6 μm or less.

3. The image pickup module according to claim 1, wherein the surface coarseness Ra of the inner circumferential surface of said flange part is 0.2 μm or less.

4. The image pickup module according to claim 1, wherein an angle θ made by a perpendicular to the inclined surface and an image pickup surface of the image pickup element satisfies the limitation $$\sin\theta \geq (1/n)$$

where n is the refractive index of the lens having said flange part.

5. The image pickup module according to claim 4, wherein the lens having said flange part is manufactured by an injection molding of resin, and the refractive index of said resin is 1.49 or more.

6. The image pickup module according to claim 4, wherein the lens having said flange part is manufactured by an injection molding of resin, and the refractive index of said resin is 1.56 or more.

7. An endoscope that includes the image pickup module according to claim 1.

8. A capsule-type endoscope that includes the image pickup module according to claim 1.

9. An endoscope that includes the image pickup module according to claim 4.

10. A capsule-type endoscope that includes the image pickup module according to claim 4.

11. The image pickup module according to claim 1, wherein the flange part and the illumination elements are arranged in such a manner that the exposed portion, which fails to be shaded by the frame component, of the flange part is located closer to an image side than are the light-emitting surfaces of the illumination elements.

12. The image pickup module according to claim 1, wherein, in the light-emitting surfaces of the illumination elements, regions from which emergent light is reachable to the exposed portion of the flange part are shaded by light-intercepting members.

13. The image pickup module according to claim 1, wherein the lens having the flange part and the image pickup element are made fixed to each other by application of an optical hardening adhesive to a portion where the top portion of the flange part and the image pickup element meet and subsequent hardening of the optical hardening adhesive caused by introduction of light, through a gap between a top portion of the frame component and the image pickup element, into the portion where the top portion of the flange part and the image pickup element meet.

14. The image pickup module according to claim 1, wherein a gap between a top portion of the frame component and the image pickup element is sealed with an adhesive having a light intercepting function.

15. A manufacturing method of an image pickup module that includes
    (a) a lens having a flange part, said lens and flange part being integrally formed of a light transmitting material,
    (b) an image pickup element that touches a top portion of the flange part, with an inner circumferential surface of the flange part having an inclined surface such that a diameter of the inner circumferential surface becomes larger as the inclined surface approaches said image pickup element,
    (c) a frame component that forms a lens assembly together with the lens having the flange part, the frame component being constructed and arranged to shade an outer circumferential surface of the lens excluding a neighborhood of the top portion of the flange part, and
    (d) illumination elements arranged around the lens assembly and the image pickup element, wherein
    the image pickup module is constructed and arranged so that light emergent from light-emitting surfaces of the illumination elements fails to directly reach an exposed portion, which fails to be shaded by the frame component, of the flange part, and
    after the top portion of the flange part has been fixed by touching the image pickup element, a lens surface at the object side of the lens having the flange part is coated.

16. An assembling method of an image pickup module that includes
    a lens having a flange part, said lens and flange part being integrally formed of a light transmitting material by injection molding;
    an image pickup element which a top portion of the flange part touches;
    a frame component that forms a lens assembly together with the lens having the flange part, the frame component being constructed and arranged to shade an outer circumferential surface of the lens excluding a neighborhood of the top portion of the flange part;
    an inner circumferential surface of the flange part has an inclined surface such that a diameter of the inner circumferential surface becomes larger as the inclined surface approaches said image pickup element; and
    illumination elements arranged around the lens assembly and the image pickup element wherein
    the image pickup module is constructed and arranged so that light emergent from light-emitting surfaces of the illumination elements fails to directly reach an exposed portion which fails to be shaded by the frame component, of the flange part,
    said assembling method comprising the following steps, performed in the order indicated:
    (a) a first cutting process for cutting gate mark in said lens having a flange part integrally formed by injection molding so that a predetermined length of said gate mark in a radial direction of said lens remain, from a position that does not contain the gate mark;

(b) a touching process for touching a top portion of the flange part to an image pickup element after said first cutting process; and (c) a second cutting process for cutting again said gate mark so as to shorten said predetermined length.

17. The assembling method according to claim 16 wherein, in step (b), while gripping said gate mark that was cut in step (a), said flange part touches said image pickup element.

18. The assembling method according to claim 16 wherein, between steps (b) and (c), there is a step of attaching a predetermined optical element to said lens having a flange part.

19. The assembling method according to claim 16, wherein, between steps (a) and (b), there is a step of attaching a predetermined optical element to said lens having a flange part.

20. The assembling method according to claim 16, wherein the cutting of a gate mark in said first cutting process is carried out at a predetermined position which is separated radially by 1 mm or more from a position that does not contain the gate mark; and the cutting of a gate mark in said second cutting process is carried out at a predetermined position where an amount of projection of the gate mark from the assembling component of the lens is 0.3 mm or less.

21. The assembling method of an image pickup module according to claim 16, and further comprising:

(d) applying an adhesive or paint having a light blocking function to said gate mark after step (c).

22. An image pickup module that has been assembled as per claim 16, wherein a cut surface of a gate mark, that is formed when the injection molding is carried out, is inclined to a surface that is perpendicular to the direction of a long side of the gate mark.

23. The image pickup module according to claim 22, wherein an adhesive or paint having a light blocking function is applied to the cut surface of said gate mark.

24. An image pickup module comprising:
a lens having a flange part, said lens and flange part being integrally formed of a light transmitting material;
an image pickup element which a top part of the flange part touches;
illumination elements arranged around said lens;
a frame component that forms a lens assembly together with the lens having the flange part, the frame component being constructed and arranged to shade an outer circumferential surface of the lens excluding a neighborhood of the top portion of the flange part;
an inner circumferential surface of the flange part has an inclined surface such that a diameter of the inner circumferential surface becomes larger as the inclined surface approaches said image pickup element; and
the illumination elements arranged around the lens assembly and the image pickup element; wherein
the image pickup module is constructed and arranged so that light emergent from light-emitting surfaces of the illumination elements fails to directly reach an exposed portion, which fails to be shaded by the frame component, of the flange part, and
when the image pickup module is viewed from a direction of a center axis of the lens, the illumination elements are shown at positions off a line that originates from the center axis of the lens and passes through a center of a gate mark remaining on the lens.

25. The image pickup module according to claim 24, wherein, when the image pickup module is viewed from the direction of the center axis of the lens, the illumination elements are shown at positions off any line that originates from the center axis of the lens and passes through any point, between end to end, of the gate mark.

26. An image pickup module comprising:
a lens assembly comprising a lens having a flange part and a frame component, said lens and flange part being integrally formed of a light transmitting material, said frame component constructed and arranged to shade an outer circumferential surface of the lens excluding a neighborhood of a top portion of the flange part;
an image pickup element which the top portion of the flange part touches;
an inner circumferential surface of the flange part has an inclined surface such that a diameter of the inner circumferential surface becomes larger as the inclined surface approaches said image pickup element; and
illumination elements arranged around the lens assembly and the image pickup element;
wherein the image pickup module is constructed and arranged so that light emergent from light-emitting surfaces of the illumination elements fails to directly reach an exposed portion, which fails to be shaded by the frame component, of the flange part, and
in the light-emitting surfaces of the illumination elements, regions from which emergent light is reachable to the exposed portion of the flange part are shaded by light intercepting members of the illumination elements.

* * * * *